(12) United States Patent
Johnson (10) Patent No.: US 8,297,318 B2
(45) Date of Patent: Oct. 30, 2012

(54) CHECK VALVE

(76) Inventor: Mark Johnson, Sandy, UT (US)

( * ) Notice: Subject to any disclaimer, the term of this patent is extended or adjusted under 35 U.S.C. 154(b) by 1447 days.

(21) Appl. No.: 11/248,900

(22) Filed: Oct. 11, 2005

(65) Prior Publication Data

US 2006/0260703 A1 Nov. 23, 2006

Related U.S. Application Data

(60) Provisional application No. 60/683,477, filed on May 21, 2005.

(51) Int. Cl.
*F16K 15/14* (2006.01)

(52) U.S. Cl. ............ 137/854; 137/516.17; 137/526

(58) Field of Classification Search ............ 137/516.19, 137/516.17, 844, 854, 843, 526, 601.2
See application file for complete search history.

(56) References Cited

U.S. PATENT DOCUMENTS

| | | | | |
|---|---|---|---|---|
| 2,859,771 | A | * | 11/1958 | Blagg ............ 137/512.15 |
| 3,473,561 | A | * | 10/1969 | Svenson et al. ............ 137/854 |
| 3,860,042 | A | | 1/1975 | Green |
| 3,911,949 | A | * | 10/1975 | Hilden et al. ............ 137/854 |
| 3,949,780 | A | | 4/1976 | Buckman |
| 3,993,060 | A | | 11/1976 | Mitchell |
| 4,032,106 | A | | 6/1977 | Schieser et al. |
| 4,066,077 | A | | 1/1978 | Shamlian |
| 4,071,024 | A | | 1/1978 | Blanc |
| 4,137,935 | A | | 2/1979 | Snowdon |
| 4,143,853 | A | | 3/1979 | Abramson |
| 4,230,240 | A | | 10/1980 | Laauwe |
| 4,278,080 | A | | 7/1981 | Schuch |
| 4,344,427 | A | | 8/1982 | Marvin |
| 4,523,610 | A | | 6/1985 | Orrico |
| 4,562,836 | A | | 1/1986 | Perron |
| 4,610,246 | A | | 9/1986 | Delphia |
| 4,655,212 | A | | 4/1987 | Delphia |
| 4,708,135 | A | | 11/1987 | Arkema |
| 4,731,075 | A | | 3/1988 | Gallo Mezo et al. |
| 4,782,830 | A | | 11/1988 | Forman |
| 4,793,341 | A | | 12/1988 | Arasmith |
| 4,805,610 | A | | 2/1989 | Hunt |

(Continued)

FOREIGN PATENT DOCUMENTS

GB 1357249 6/1974

(Continued)

OTHER PUBLICATIONS

U.S. Appl. No. 10/453,462, filed Jun. 3, 2003, Johnson.

(Continued)

*Primary Examiner* — Kevin Lee
*Assistant Examiner* — Macade Brown
(74) *Attorney, Agent, or Firm* — Dax D. Anderson; Kirton McConkie (57) ABSTRACT

A check valve made up of a substantially rigid portion and a substantially flexible membrane that is generally dome shaped. The substantially rigid portion includes one or more spokes that meet in the center of the rigid portion and one or more partial spokes extending part way to the center of the rigid portion. The dome shaped, substantially flexible membrane also includes one or more flexible spokes and one or more collapse zones. The completed check valve is made by connecting a center portion of the substantially rigid portion to a center portion of the dome shaped, substantially flexible membrane.

30 Claims, 5 Drawing Sheets

U.S. PATENT DOCUMENTS

| | | | |
|---|---|---|---|
| 4,832,013 A | 5/1989 | Hartdom |
| 4,834,084 A | 5/1989 | Walsh |
| 4,860,739 A | 8/1989 | Vandepol |
| 4,862,903 A | 9/1989 | Campbell |
| 4,872,453 A | 10/1989 | Christianson |
| 4,877,022 A | 10/1989 | Christianson |
| 4,878,491 A | 11/1989 | McGilvray, III |
| 4,879,995 A | 11/1989 | Christianson |
| 4,884,564 A | 12/1989 | Lamont |
| 4,896,664 A | 1/1990 | Harayama |
| 4,907,582 A | 3/1990 | Meyerrose |
| 4,938,259 A | 7/1990 | Schmidt |
| 4,946,133 A | 8/1990 | Johnson et al. |
| 5,020,191 A | 6/1991 | Uke |
| 5,101,818 A | 4/1992 | Chace |
| 5,117,817 A | 6/1992 | Lin |
| 5,129,426 A | 7/1992 | Boehmer |
| 5,143,059 A | 9/1992 | Delphia |
| 5,199,422 A | 4/1993 | Rasocha |
| 5,231,982 A | 8/1993 | Harrison et al. |
| 5,245,997 A | 9/1993 | Bartos |
| 5,261,396 A | 11/1993 | Faulconer et al. |
| 5,265,591 A | 11/1993 | Ferguson |
| 5,267,556 A | 12/1993 | Feng |
| 5,271,432 A | 12/1993 | Gueret |
| 5,280,785 A | 1/1994 | Fujima |
| 5,297,545 A | 3/1994 | Infante |
| 5,327,849 A | 7/1994 | Miller |
| 5,357,654 A | 10/1994 | Hsing-Chi |
| 5,381,563 A | 1/1995 | Isabelle et al. |
| 5,398,673 A | 3/1995 | Lambert |
| 5,404,872 A | 4/1995 | Choi |
| 5,487,379 A | 1/1996 | Koshiishi |
| 5,518,026 A | 5/1996 | Benjey |
| 5,529,057 A | 6/1996 | Ferrero |
| 5,606,967 A | 3/1997 | Wang |
| 5,622,165 A | 4/1997 | Huang |
| 5,638,811 A | 6/1997 | David |
| 5,657,746 A | 8/1997 | Christianson |
| 5,664,558 A | 9/1997 | Wagoner |
| 5,671,728 A | 9/1997 | Winefordner |
| 5,697,362 A | 12/1997 | Albrecht |
| 5,791,524 A | 8/1998 | Demarest |
| 5,865,169 A | 2/1999 | Lan |
| 5,868,129 A | 2/1999 | Christianson |
| D406,333 S | 3/1999 | Garraffa |
| 5,893,362 A | 4/1999 | Evans |
| 5,906,199 A | 5/1999 | Budzinski |
| 5,924,416 A | 7/1999 | Miller |
| 5,937,850 A | 8/1999 | Kawashima |
| 5,947,116 A | 9/1999 | Gamow |
| 5,960,791 A | 10/1999 | Winefordner |
| 6,059,157 A | 5/2000 | Parsons et al. |
| 6,073,626 A | 6/2000 | Riffe |
| 6,079,410 A | 6/2000 | Winefordner et al. |
| 6,085,744 A | 7/2000 | Hermansen et al. |
| 6,119,685 A | 9/2000 | Kawashima |
| 6,123,320 A | 9/2000 | Rasanow et al. |
| 6,129,081 A | 10/2000 | Wu |
| 6,129,116 A | 10/2000 | Laskowski |
| 6,202,644 B1 | 3/2001 | Takeuchi |
| 6,240,962 B1 | 6/2001 | Tai et al. |
| 6,273,046 B1 | 8/2001 | Pierce |
| 6,276,362 B1 | 8/2001 | Chen-Lieh |
| 6,302,102 B1 | 10/2001 | Giroux |
| 6,318,363 B1 | 11/2001 | Monnich |
| 6,352,075 B1 | 3/2002 | Wang |
| 6,363,929 B1 | 4/2002 | Winefordner |
| 6,371,108 B1 | 4/2002 | Christianson |
| 6,394,417 B1 | 5/2002 | Browne et al. |
| 6,401,711 B1 | 6/2002 | Tibbs |
| 6,435,178 B1 | 8/2002 | Lin |
| 6,478,024 B1 | 11/2002 | White |
| 6,513,520 B2 | 2/2003 | Vinokur et al. |
| 6,575,191 B2 * | 6/2003 | Skeens et al. ............ 137/512.15 |
| 6,655,378 B2 | 12/2003 | Swetish |
| 6,709,604 B2 | 3/2004 | Tai et al. |
| 6,736,136 B2 | 5/2004 | Chen-Lieh |
| 6,827,105 B1 | 12/2004 | Marble et al. |
| 6,832,706 B2 | 12/2004 | Hearld et al. |
| 6,883,780 B2 | 4/2005 | Browne et al. |
| 6,908,210 B2 | 6/2005 | Kuo |
| 6,915,801 B2 | 7/2005 | Pokras |
| 7,182,093 B2 * | 2/2007 | Call et al. ................... 137/15.18 |
| 7,185,796 B2 | 3/2007 | Parsons |
| 2002/0088460 A1 | 7/2002 | Monnich |
| 2002/0170558 A1 | 11/2002 | Vinokur |
| 2003/0029448 A1 | 2/2003 | Swetish |
| 2003/0037783 A1 | 2/2003 | Feng |
| 2004/0035414 A1 | 2/2004 | Johnson |
| 2005/0034726 A1 | 2/2005 | Pittaway et al. |
| 2006/0102176 A1 | 5/2006 | Junck |
| 2006/0272637 A1 | 12/2006 | Johnson |

FOREIGN PATENT DOCUMENTS

| | | |
|---|---|---|
| GB | 1434835 | 5/1976 |
| GB | 2171781 | 9/1986 |
| GB | 2313317 | 11/1997 |
| JP | 09-032722 | 2/1997 |
| JP | 10-299922 | 11/1998 |
| JP | 2002-154480 | 5/2002 |
| JP | 2004-169748 | 6/2004 |
| TW | 365525 | 8/1999 |
| TW | 200306273 | 11/2003 |
| TW | 573667 | 1/2004 |
| TW | M248730 | 11/2004 |
| TW | M252649 | 12/2004 |
| WO | WO 92/22342 | 12/1992 |
| WO | WO 2006/042063 | 4/2006 |
| WO | WO 2006/127556 | 11/2006 |
| WO | WO 2006/127557 | 11/2006 |

OTHER PUBLICATIONS

U.S. Appl. No. 11/244,522, filed Oct. 6, 2005, Johnson.
U.S. Appl. No. 11/437,113, filed May 18, 2006, Johnson.
U.S. Appl. No. 11/923,423, filed Oct. 24, 2007, Johnson.
Fee et al., "Cardiorespiratory responses to increased resistance during exercise," Lung Mechanics, 5032.
Ellingsen, "The influence on the breathing pattern in man of moderate levels of continuous positive and negative airway pressure and of positive end-expiratory pressure during air and $CO_2$ inhalation," ACTA Physiol Scand 1990, 138, 273-282.
Van Der Shans, "Effect of positive expiratory pressure on breathing pattern in healthy subjects," Eur Respir J, 1993, 6, 60-66.
Layon et al., "Continuous positive airway pressure and expiratory positive airway pressure increase functional residual capacity equivalently," CHEST, 89/4/Apr. 1986, p. 517.
Tobin et al., "Effect of positive end-expiratory pressure on breathing patterns of normal subjects and intubated patients with respiratory failure," Critical Care Medicine, 1983, p. 859, vol. 11-No. 11, Williams & Wilkins Co.
Savourey et al., "Postive end expiratory pressure (PEEP) slightly modifies ventilatory response during incremental exercise," Aviation, Space and Environmental Medicine, Jan. 2001, p. 21, vol. 72-No. 1.
Muller, "A field study of the ventilatory response to ambient temperature and pressure in sport diving," Br. J. Sports Med., 1995, vol. 29, No. 3, p. 185-190, Butterworth Heinemann.
Office Action dated Sep. 11, 2007 from U.S. Appl. No. 10/453,462, 13 pages.
Office Action dated Feb. 23, 2006 from U.S. Appl. No. 10/453,462, 11 pages.
Office Action dated Jun. 23, 2005 from U.S. Appl. No. 10/453,462, 13 pages.
Office Action dated Mar. 21, 2005 from U.S. Appl. No. 10/453,462, 5 pages.
Office Action dated Oct. 17, 2007 from U.S. Appl. No. 11/244,522, 8 pages.
Office Action dated May 24, 2007 from U.S. Appl. No. 11/244,522, 5 pages.
International Search Report from PCT/US2005/036072 dated Dec. 8, 2006, 2 pages.
International Preliminary Report on Patentability from PCT/US2005/036072 dated Apr. 11, 2007, 6 pages.

Written Opinion from PCT/US2005/036072 dated Sep. 25, 2006, 5 pages.
Office Action dated Aug. 23, 2006 from U.S. Appl. No. 11/244,522, 7 pages.
International Search Report from PCT/US2006/019658 dated Dec. 13, 2006, 2 pages.
International Preliminary Report on Patentability from PCT/US2006/019658 dated Nov. 23, 2007, 4 pages.
Written Opinion from PCT/US2006/019658 dated Oct. 28, 2006, 3 pages.
International Search Report from PCT/US2006/019659 dated Jul. 27, 2007, 2 pages.
International Preliminary Report on Patentability from PCT/US2006/019659 dated Nov. 23, 2007, 5 pages.
Written Opinion from PCT/US2006/019659 dated May 29, 2007, 4 pages.
U.S. Appl. No. 12/034,617, filed Feb. 20, 2008, Johnson.
International Search Report and Written Opinion from PCT/US2007/082520, dated May 7, 2008, 10 pages.
Search Report from Taiwan Application No. 095118125, dated Feb. 18, 2005, 1 page.
Search Report from Taiwan Application No. 095118124, dated Oct. 17, 2008, 1 page.
International Search Report and Written Opinion from PCT/US2008/054475, dated Aug. 15, 2008, 11 pages.
Office Action from Chinese Patent Application No. 2006800176981, dated Apr. 24. 2009, 9 pages.
Office Action from Australian Patent Application No. 2006251592, dated May 7, 2009, 1 page.
Office Action from Australian Patent Application No. 2006251593, dated May 19, 2009, 2 pages.
Examination Report for Singapore Patent Application No. 200717891-6, dated Jan. 29, 2009, 5 pages.
International Preliminary Report on Patentability from PCT/US0228/054475, dated Aug. 26, 2009, 8 pages.
Examination Report from Canadian Patent Application No. 2,609,479, dated Aug. 27, 2009, 4 pages.
Examination Report from Canadian Patent Application No. 2,609,204 dated Sep. 23, 2009, 2 pages.
Examination Report from New Zealand Patent Application No. 563367 dated Aug. 18, 2009, 2 pages.
Examination Report from New Zealand Patent Application No. 563368 dated Aug. 19, 2009, 2 pages.
European Search Report from EPO Patent Application No. 06770786.9 dated Aug. 5, 2009, 6 pages.
Office Action dated Oct. 4, 2010 from U.S. Appl. No. 12/034,617.
Office Action dated Oct. 5, 2010 from U.S. Appl. No. 11/437,113.
Office Action dated Jan. 20, 2011 from U.S. Appl. No. 11/923,423.
Notice of Allowance dated Apr. 19, 2011 from U.S. Appl. No. 12/034,617.
Examination Report dated Mar. 11, 2011 from New Zealand Application No. 563367.
Examination Report dated Mar. 14, 2011from New Zealand Application No. 563368.
Notice of Allowability from U.S. Appl. No. 11/244,522, dated May 14, 2010.
Notice of Allowability from U.S. Appl. No. 10/453,462, dated May 14, 2010.

* cited by examiner

// CHECK VALVE

CROSS REFERENCE TO RELATED APPLICATIONS

This application claims priority to and the benefit of U.S. Provisional Patent Application Ser. No. 60/683,477, entitled VALVES, BAFFLES, SHORTENED SNORKELS, STEALTH SNORKELS, SNORKEL EQUIPMENT COMBINED WITH SCUBA EQUIPMENT, which was filed on May 21, 2005, and is hereby incorporated by reference in its entirety.

BACKGROUND OF INVENTION

1. Field of Invention

The present invention generally relates valves and, in particular, to check valves that may be used to allow fluid to flow in one direction and prevent fluid from flowing in an opposite direction.

2. Description of Related Art

Conventional check valves are devices that allow gases, liquids or other fluids to flow in one direction. In particular, conventional check valves allow fluid to flow in a desired direction when sufficient pressure or force acts on the check valve. Conventional check valves, however, prevent fluid from flowing through the valve in an undesired direction. Specifically, when these pressures and forces are such that the flow of the fluid would be in the undesired direction, the check valve automatically closes resulting in the stopping or checking of the flow in this undesired direction.

Some known check valves use a flexible membrane that functions as a diaphragm. This diaphragm is designed to deform or bend in order to allow flow of fluid in a desired direction. This diaphragm may also return to its original position in order to prevent flow in the opposite direction.

Check valves have a positive pressure differential when there is greater pressure upstream from the check valve, in the desired direction of flow, than there is downstream from the check valve. In contrast, check valves have a negative pressure differential when there is greater pressure downstream from the check valve than there is upstream. If a positive pressure differential exists and it is sufficient in its magnitude, then the diaphragm may bend to create a space or passage through which fluid can flow through the check valve in the desired direction. The minimum pressure, or pressure differential, required to open a check valve is sometimes referred to as the cracking pressure. If no pressure differential or a negative pressure differential exists, or if a positive pressure differential exists but is insufficient in magnitude, then the diaphragm will prevent the flow of fluid through the check valve. In particular, the diaphragm will bend or deflect from its original or normal position to allow fluid to flow when there is a sufficient positive pressure differential. When there is no longer a sufficient positive pressure differential, then the diaphragm will return to its original or normal position to prevent flow though the valve.

Known check valves often have several shortcomings. For instance, some conventional check valves have a high cracking pressure. That is, these check valves require a large positive pressure differential before they will open. Disadvantageously, a check valve with an undesirably high cracking pressure will prevent flow in the desired direction even through the relative forces and pressures would normally allow this desired flow. Furthermore, some conventional check valves do not close until a relatively large negative pressure differential exists. A check valve that requires a substantial negative pressure differential to close may allow an undesirable or unacceptable amount of back flow, or flow contrary to the desired direction, when negative pressure differential of a small magnitude exists.

Additionally, some conventional check valves have components or structures that interfere with or resist the flow of fluid in the desired direction when the check valve is open. These known check valves that add resistance to the flow of fluid in the desired direction may undesirably decrease the efficiency of the system. Furthermore, some conventional check valves may leak when the valve is open, allowing some of the fluid to proceed or flow in a direction contrary to the desired direction.

Some conventional check valves may also produce noises as they open and close or when they leak. In some applications, the noise may be very undesirable and disconcerting. Furthermore, many known check valves are not aesthetically pleasing in their design. In addition, some known check valves have a large size and/or may be difficult to manufacture. For example, some conventional check valves may include components that have to be manufactured to relatively tight tolerances and interconnected in a very careful and meticulous manner.

Further, some conventional check valves have a complex design with a number of parts and components. Disadvantageously, the complex design may make the check valve more difficult and costly to manufacture. Conventional check valves with a complex design may also be more difficult to clean, maintain, repair and replace. Additionally, the complex design and numerous parts of some known check valves may be more prone to failure.

BRIEF SUMMARY OF INVENTION

A need therefore exists for a check valve that eliminates the above-described disadvantages and problems.

One aspect is a check valve that may have a relatively low cracking pressure. Thus, the check valve may open to allow fluid flow in the desired direction when there is a positive pressure differential, even if the magnitude of the positive pressure differential is small.

Another aspect is a check valve that may prevent undesirable back flow through the valve. For example, the check valve may either entirely or within reasonable tolerances prevent back flow through the valve.

Still another aspect is a check valve that may not leak when it is in the closed position. That is, when the check valve is closed, it may prevent any fluid from flowing through the valve.

Yet another aspect is a check valve that may include a membrane or diaphragm. The membrane or diaphragm may be sized and configured to provide little or no resistance or interference to the flow of fluid through the valve in the desired direction.

A further aspect is a check valve which may be relatively quiet in its operation. Advantageously, this may allow the check valve to be used in a wide variety of situations and environments.

A still further aspect is a check valve which may be aesthetically pleasing in its design. In addition, the check valve may have a rather straight-forward design, which may allow it to be easily and efficiently manufactured, maintained and cleaned.

Still yet another aspect is a check valve that may be manufactured within a relatively wide range of tolerances. Significantly, the wide range of manufacturing tolerances may allow the valve to be economically manufactured. In addition, the check valve may have a low failure rate.

A further aspect is a check valve that may include a substantially flexible membrane and a substantially rigid portion. The substantially flexible membrane may be generally dome shaped and may act as a diaphragm. The substantially flexible membrane may also flex or deform in order to open the check valve. The substantially rigid portion may also be generally dome shaped and may include a surface against which the substantially flexible membrane may touch or contact. The substantially rigid portion may be sized and configured to help position and/or control the movement of the substantially flexible membrane. For example, the substantially rigid portion may be sized and configured to help close or seal the check valve. The substantially rigid portion may also help provide structural support to the substantially flexible membrane.

A still further aspect is a check valve that may include a substantially flexible membrane with a sealing edge or outer edge at its periphery and a substantially rigid portion with a sealing ring. The substantially flexible membrane may be naturally biased so that its outer edge may tend to press up against the sealing ring of the substantially rigid portion. When the outer edge of the substantially flexible membrane contacts or is pressed against the sealing ring of the substantially rigid portion, then the check valve may be closed and fluid may not be able to pass through the check valve. The valve may open when the substantially flexible membrane flexes or bends so that its outer edge separates from the sealing ring of the substantially rigid portion. When this separation occurs, an opening or passage may be created through which fluid may pass.

A yet further aspect is a check valve that may include a substantially flexible membrane which may deform when there is a positive pressure differential of a sufficient magnitude. In particular, the flexible membrane may have a dome shaped configuration with the top of the dome disposed in the direction opposite to the direction of the desired flow. Thus, the fluid may press down on the top of the dome shaped membrane and in on the sides or periphery of the dome shaped membrane when a positive pressure differential exists. If the magnitude of the pressure differential is sufficient, the pressure may cause the sides and/or outer edges of the substantially flexible membrane to move inwardly, thereby creating a gap between the outer edge of the substantially flexible membrane and the sealing ring of the substantially rigid portion. If there is no pressure differential or if the magnitude of the positive pressure differential is insufficient, the outer edge of the substantially flexible membrane may return to its normally biased position in which it preferably contacts the sealing ring of the substantially rigid portion. Additionally, if a negative pressure differential exists, then the fluid may press up on the bottom and out on the sides and outer edge of the substantially flexible membrane. This pressure may push the outer edge of the substantially flexible membrane into contact with the sealing ring of the substantially rigid portion thereby closing the valve. Closing the valve may create a seal so that the fluid may not be able to pass in between the substantially flexible membrane and the substantially rigid portion in a direction opposite the desired direction of flow.

Another aspect is a check valve which may include a substantially flexible membrane with a sealing edge at its periphery and a substantially rigid portion with a sealing ring. Because the outer edge of the substantially flexible membrane may be intended to separate from the sealing ring of the substantially rigid portion, the outer edge of the substantially flexible membrane may not be securely or permanently attached to the sealing ring of the substantially rigid portion. Rather, the substantially flexible membrane may be connected, for example, by its center, to the center of the substantially rigid portion of the check valve. When the check valve is open, fluid may pass through the valve along the valve's edge or periphery rather than through its center.

Still another aspect is a check valve which may include a substantially rigid portion with a plurality of substantially rigid spokes. For example, the spokes may extend from a generally rigid base, which may include the sealing ring, to the center portion of the check valve. These spokes may serve to attach the base to the center portion of the substantially rigid portion. In between each of these spokes may be an opening or gap through which fluid may pass. If the valve is open, the fluid may pass through these openings or gaps and then through the spaces or channels in between the outer edge of the substantially flexible membrane and the sealing ring of the substantially rigid portion.

Still another aspect is a check valve which may include a substantially flexible membrane with a plurality of relatively thin sections and a plurality of relatively thick sections which may be created as integral parts of the substantially flexible membrane. The relatively thick sections may extend from the outer rim of the substantially flexible membrane to the center portion of the substantially flexible membrane and may also resemble spokes. These relatively thick sections may provide structural support to the dome shaped, substantially flexible membrane. Preferably, the substantially flexible membrane may include a plurality of relatively thick sections, equal in number to the number of substantially rigid spokes included in the substantially rigid portion of the check valve. Furthermore, the substantially flexible membrane may be connected to the substantially rigid portion such that each of these relatively thick portions will be located generally in between two of the substantially rigid spokes. The added support provided by the relatively thick sections of the substantially flexible membrane may allow the substantially flexible membrane in general, and the relatively thin sections of the substantially flexible membrane specifically, to be manufactured to be thinner and more flexible. The flexibility of these relatively thin sections may allow the valve to open in the presence of a small positive pressure differential, thereby creating a check valve a very low cracking pressure. The flexibility of these relatively thin sections may also allow the valve to close where there is no pressure differential or a negative pressure differential, which may create a check valve with little or no back flow or leakage.

Still another aspect is a check valve that may include a substantially rigid portion with a plurality of partial spokes. The spokes may extend from a substantially rigid base towards a center portion, but the spokes preferably do not contact the center portion of the substantially rigid portion. The check valve may also include substantially rigid spokes that extend from the base to the center portion. Desirably, one of the partial spokes is placed between each of the substantially rigid spokes. Advantageously, the partial spokes may be sized and configured to add stability to the check valve. For example, the partial spokes may prevent the substantially flexible membrane from being pushed backward and out of contact with the rigid base and sealing ring. In addition, the partial spokes may not significantly obstruct fluid flow through the valve.

These and other aspects, features and advantages of the invention will become more fully apparent from the following detailed description of preferred embodiments and appended claims.

BRIEF DESCRIPTION OF DRAWINGS

The appended drawings contain figures of preferred embodiments to further clarify the above and other aspects, advantages and features of the invention. It will be appreciated that these drawings depict only preferred embodiments of the invention and are not intended to limit its scope. The invention will be described and explained with additional specificity and detail through the use of the accompanying drawings in which.

DETAILED DESCRIPTION OF PREFERRED EMBODIMENTS

It will be readily understood that the components of the present invention, as generally described and illustrated in the Figures herein, could be arranged and designed in a wide variety of different configurations. Thus, the following more detailed description of preferred embodiments is not intended to limit the scope of the invention, as claimed, but it is merely representative of some of the presently preferred embodiments of the present invention.

The present invention is generally directed towards a check valve that may be used in connection with, for example, an inhalation valve for a snorkel and a tracheostomy speaking valve. It will be understood, however, that the check valve may be used in connection with other types of devices and in other suitable environments. For instance, the check valve may be used to regulate the flow of any type of fluid or flowable materials such as air, water, blood and the like. Thus, the check valve may be used with an artificial heart valve, an intravenous valve, an irrigation valve, etc. Accordingly, while the check valve may be discussed below in connection with an inhalation valve for a snorkel or a tracheostomy speaking valve, it will be appreciated that the valve may be used in any suitable situation where it is desired to regulate flow.

Additionally, to assist in the description of the check valve, words such as top, bottom, front, rear, right and left are used to describe the accompanying figures, which are not necessarily drawn to scale. It will be appreciated, however, that the present invention can be located in a variety of desired positions—including various angles, sideways and even upside down. A detailed description of the check valve now follows.

As discussed below and shown in the accompanying figures, the check valve may be used in connection with a snorkel. For example, the check valve may be an inhalation valve for a snorkel and the valve may be placed on the top of a snorkel riser tube. The check valve may open when the user of the snorkel inhales to allow the user of the snorkel to breathe surface air. The valve may then close when the user of the snorkel is not inhaling, as during exhalation or between breaths. When the valve it closed, it may prevent splash water from entering the inhalation tube of the snorkel and may prevent exhaled air from passing back through the inhalation tube thereby channeling it through the proper exhalation tube.

As best seen in FIGS. 1A through 1D, the check valve may include a substantially rigid portion 12, which may also be referred to as a substantially rigid top cap. The substantially rigid portion 12 may be constructed from a generally hard and rigid material, such as plastic, in order to provide the check valve with structural support. The check valve may also include a substantially flexible membrane 14, as best seen in FIGS. 2A through 2D. The substantially flexible membrane 14 may be constructed from a flexible or pliable material such as silicon or rubber so that it may flex or deform. The substantially flexible membrane 14 may also act as a diaphragm and it may allow the valve to open and close. In addition, the substantially flexible membrane may be biased, if desired, so that the valve tends to remain in the open or closed position. One of ordinary skill in the art will appreciate that the substantially rigid portion 12 is preferably more rigid than the substantially flexible membrane 14. One of ordinary skill in the art will also appreciate that the rigidity of the substantially rigid portion and the flexibility of the substantially flexible membrane 14 may vary depending, for example, upon the desired characteristics of the check valve. Additionally, one of ordinary skill in the art will appreciate that the substantially rigid portion 12 and the substantially flexible membrane may be constructed from other suitable materials with the desired properties.

Figure 1A:
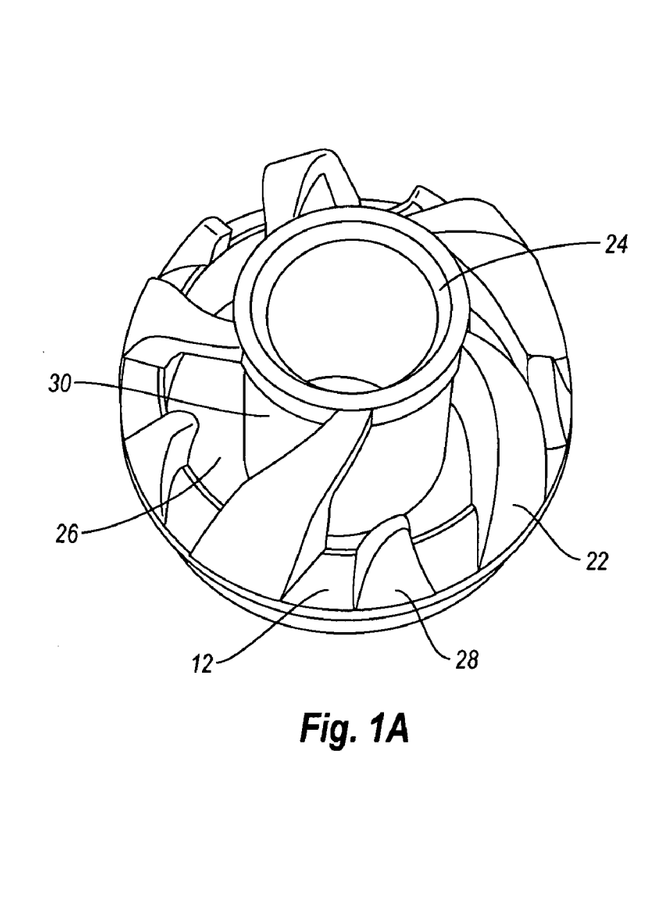
FIG. 1A is a perspective view of a portion of an exemplary embodiment of a check valve, illustrating a substantially rigid top cap.
Figure 1B:
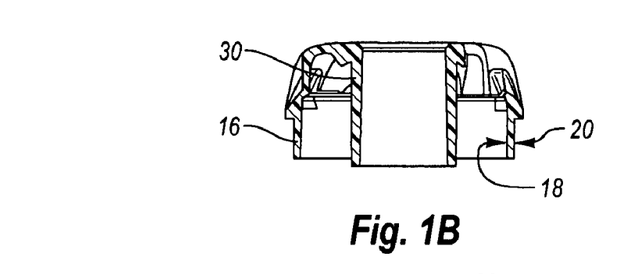
FIG. 1B is a cross-sectional side view, along lines 1B-1B shown in FIG. 1C, of the substantially rigid top cap shown in FIG. 1A.
Figure 1C:
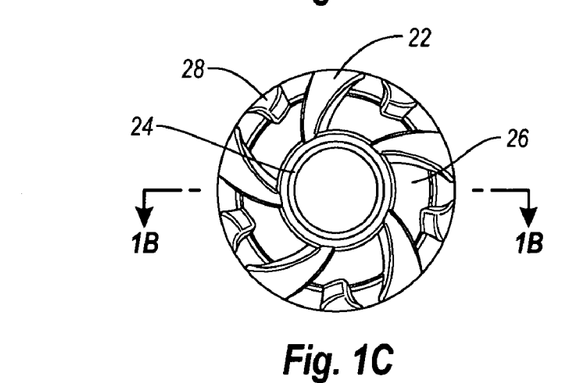
FIG. 1C is a top view of the substantially rigid top cap shown in FIG. 1A.
Figure 1D:
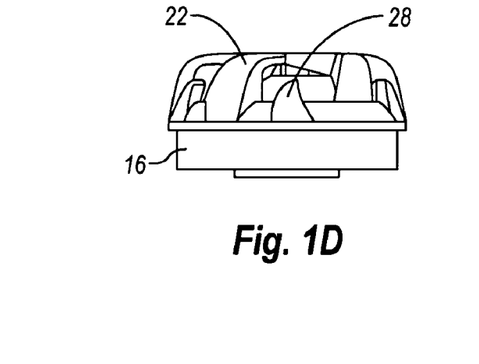
FIG. 1D is a side view of the substantially rigid top cap shown in FIG. 1A.
Figures 2A, 2B, 2C, 2D:
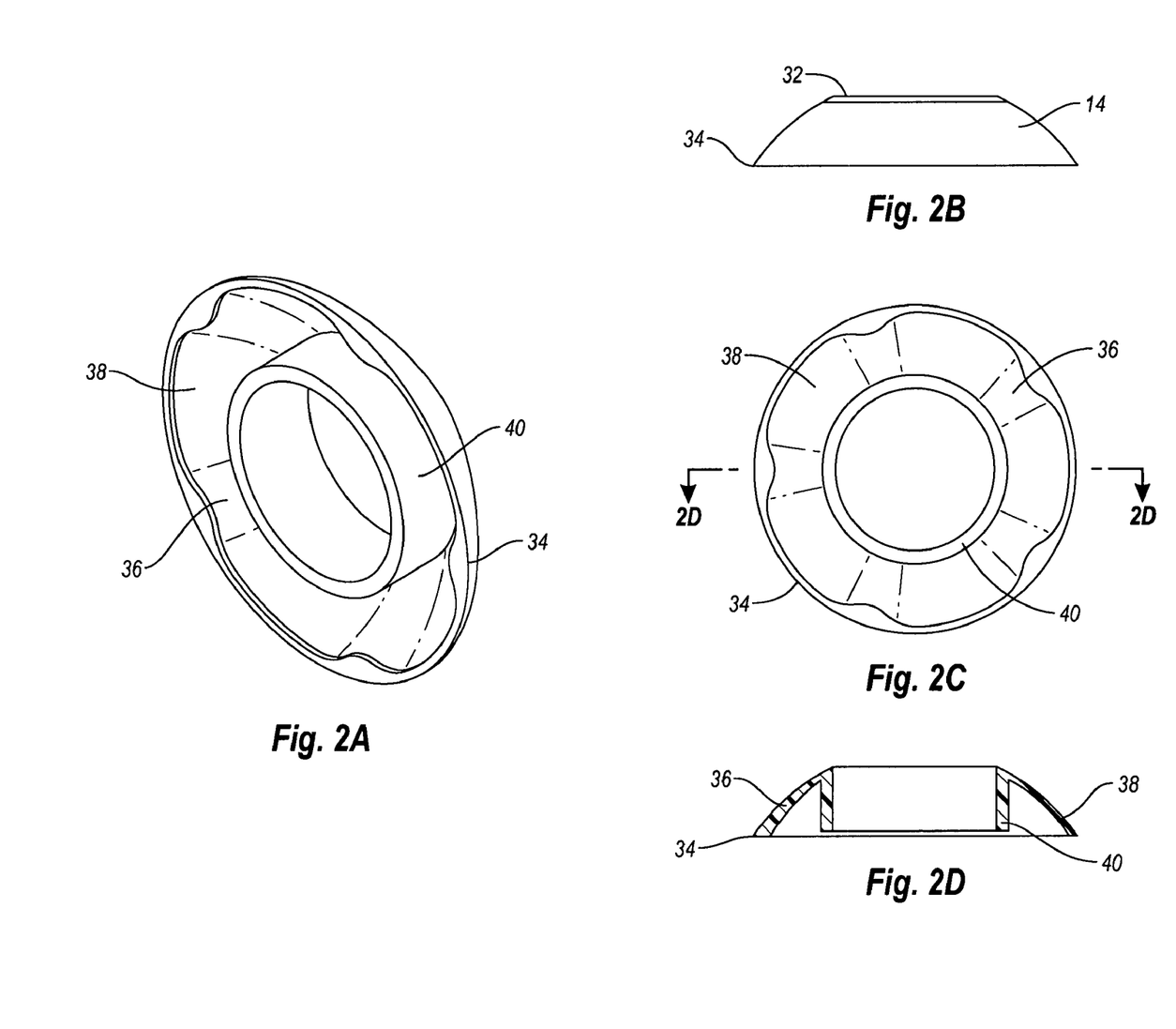
FIG. 2A is a perspective view of another portion of an exemplary embodiment of a check valve, illustrating a substantially flexible membrane.
FIG. 2B is a side view of the substantially flexible membrane shown in FIG. 2A.
FIG. 2C is a bottom view of the substantially flexible membrane shown in FIG. 2A.
FIG. 2D is a cross-sectional side view, along lines 2D-2D shown in FIG. 2C, of the substantially flexible membrane shown in FIG. 2A.
Figure 3:
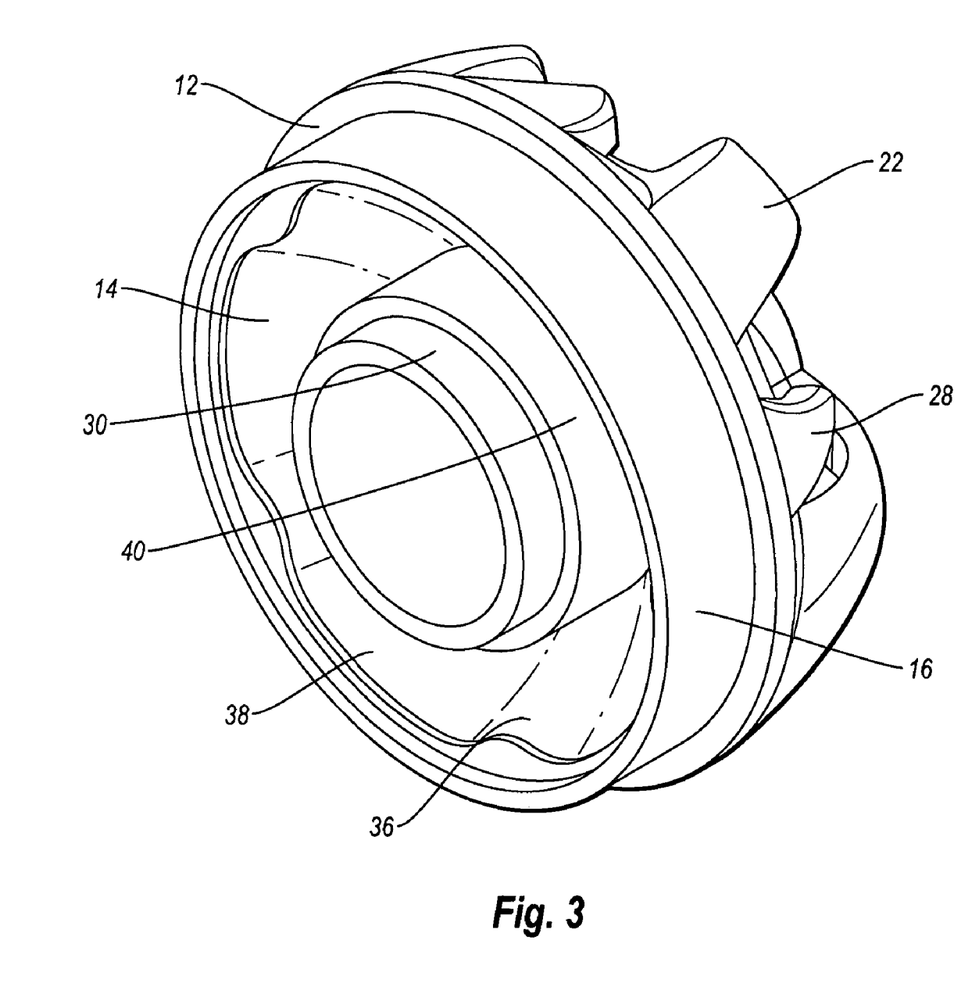
FIG. 3 is a perspective view of an exemplary embodiment of a check valve, illustrating a substantially flexible membrane attached to a substantially rigid top cap.
Figure 4A:
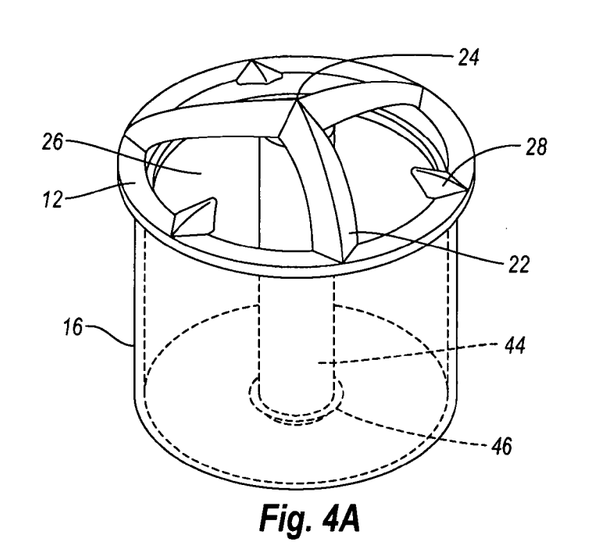
FIG. 4A is a perspective view of a portion of another exemplary embodiment of a check valve, illustrating a substantially rigid top cap.
Figure 4B:
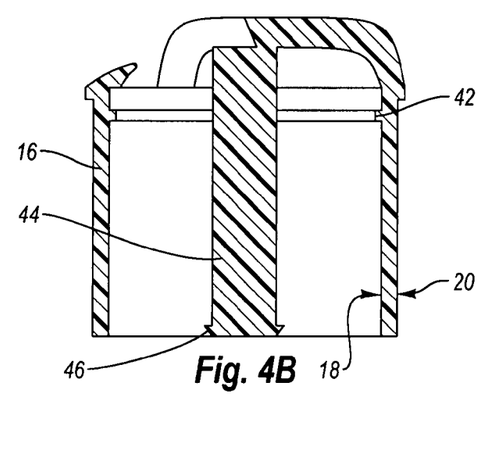
FIG. 4B is a cross-sectional side view, along lines 4B-4B shown in FIG. 4C, of the substantially rigid top cap shown in FIG. 4A.
Figure 4C:
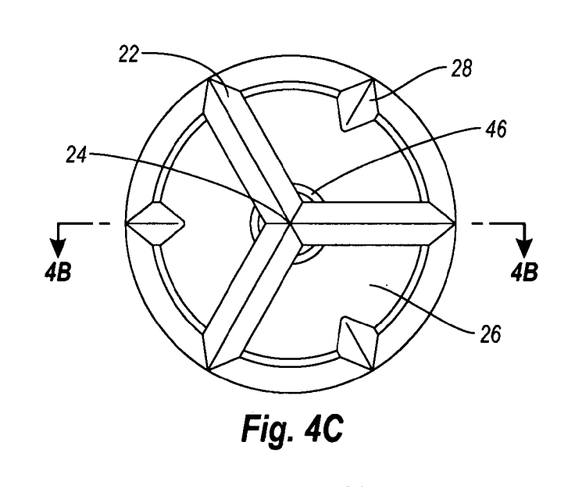
FIG. 4C is a top view of the substantially rigid top cap shown in FIG. 4A.
Figure 4D:
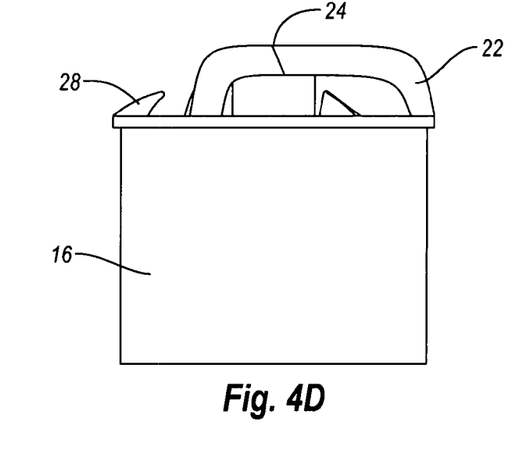
FIG. 4D is a side view of the substantially rigid top cap shown in FIG. 4A.

As shown in FIG. 3, an exemplary check valve 10 may include the substantially rigid portion 12 and the substantially flexible membrane 14. As discussed in greater detail below, the check valve 10 may be used to help control the flow of fluid in any suitable type of structure or device.

In greater detail, as shown in FIGS. 1A through 1D, the substantially rigid top cap 12 may include a substantially rigid base 16 that is preferably circular or ring shaped. The inner surface of the substantially rigid base 16 may include a sealing surface 18, sometimes referred to as a sealing ring 18, and the outer surface of the substantially rigid base 16 may include an outer rim 20. The sealing surface 18 may be the surface of the substantially rigid top cap 12 which the substantially flexible membrane 14 contacts in order to close the check valve and prevent air or water from passing in between the substantially flexible membrane 14 and the sealing ring 18. The outer rim 20 may be the portion of the substantially rigid top cap 12 which is attached or connected to the inhalation tube of the snorkel in order to hold the check valve in place.

Still referring now to FIGS. 1A through 1D, the substantially rigid top cap 12 may include a plurality of substantially rigid spokes 22. Although the substantially rigid top cap 12 illustrated in FIGS. 1A through 1D includes five rigid spokes 22, one of ordinary skill in the art will appreciate that any number of substantially rigid spokes, from a single substantially rigid spoke to a great many substantially rigid spokes, may be used. The plurality of substantially rigid spokes 22 may be connected to the substantially rigid base 16 of the substantially rigid top cap 12 and may extend upwardly and inwardly until they meet at or contact a center portion 24 of the substantially rigid top cap 12. The plurality of generally rigid spokes 22 may give the substantially rigid top cap 12 the general shape of a dome as they curve upward and inward from the substantially rigid base 16 to the center portion 24. The spokes 22 may be integrally formed with the rigid top cap 12 as part of a unitary, one-piece structure, if desired. The spokes 22 may also be separate components that are attached to the top cap 12.

The shape and positioning of the substantially rigid spokes 22 preferably creates a generally dome-shaped substantially rigid top cap 12. Advantageously, the generally dome-shaped top cap 12 may better support and mate with the substantially flexible membrane 14, which may also be generally dome shaped. It will be appreciated, however, that the substantially rigid top cap 12 and/or the substantially flexible membrane 14 may have other suitable shapes and configurations.

Still referring to FIGS. 1A through 1D, the substantially rigid top cap 12 may include a plurality of gaps 26. Each one of these gaps 26 may be positioned in between two of the plurality of substantially rigid spokes 22 so that each gap 26 may be bounded on the sides by two substantially rigid spokes 22 and on the bottom by the substantially rigid base 16. These gaps 26 are preferably sized and configured to allow fluid to pass through the substantially rigid top cap 12 of the check valve. Specifically, if the check valve is in the open position, then fluid may be allowed to pass through the space between the substantially flexible membrane 14 and the sealing ring 18 of the substantially rigid top cap 12 and into the gaps 26.

Still referring to FIGS. 1A through 1D, the substantially rigid top cap 12 may include a plurality of partial spokes 28. These partial spokes 28, like the substantially rigid spokes 22, may also be substantially rigid and may also extend upwardly from the substantially rigid base 16 of the substantially rigid top cap 12. The partial spokes 28, however, may only extend upwardly and inwardly a small distance and the partial spokes preferably do not contact each other or the center portion 24 of the substantially rigid top cap 12. By protruding up from the rigid base 16, these partial spokes 28 may provide additional support to the substantially flexible membrane 14. For example, the partial spokes 28 may provide support to the substantially flexible membrane 14 at an area where the substantially flexible membrane is not attached to the substantially rigid top cap 12. Because the partial spokes 28 preferably do not all the way to the center portion 24 of the substantially rigid top cap 12, the partial spokes may not substantially restrict or impact the flow of fluid through the gaps 26. It will be appreciated that the substantially rigid top cap 12 may include any suitable number and configuration of spokes 22 and partial spokes 28 depending, for example, upon the intended use of the valve. For example, in some situations, it may be desirable to use a greater or lesser number of spokes 22 and/or partial spokes 28, including zero.

Still referring to FIGS. 1A through 1D, the substantially rigid top cap 12 may include a center portion 24. The substantially rigid top cap 12 may also include a center cylinder 30, preferably with a generally cylindrical configuration, which may extend downwardly from the center portion 24 of the substantially rigid top cap 12. This center cylinder 30 may allow the substantially flexible membrane 14 to be attached to the center portion 24 of the substantially rigid top cap 12. As shown in the accompanying figures, the center portion 24 and the center cylinder 30 may have an opening or hole to allow the unimpeded passage of fluid. The center portion 24 and the center cylinder 30 may also be sized and configured to prevent fluid flow, if desired. Accordingly, depending upon the intended use of the check valve, the center portion 24 and the center cylinder 30 may allow any desired amount of fluid flow. In addition, the center portion 24 and the center cylinder 30 could have other suitable sizes and configurations depending, for example, upon the intended use of the check valve.

As mentioned above, one exemplary embodiment of this valve may be used as an inhalation valve for a snorkel. The snorkel which this check valve may be used on may include an exhalation tube within a larger inhalation tube. When the inhalation valve is fit onto this snorkel, the inhalation tube may fit onto or attach to the outer rim 20 of the substantially rigid base 16 of the substantially rigid top cap 12 and the exhalation tube may fit onto or be attached to the center cylinder 30 of the substantially rigid top cap 12. When the inhalation valve is attached to a snorkel in such a manner, the check valve may allow the user to inhale surface air through the inhalation tube only when it is open and only in the check valve's desired direction of flow. Air exhaled through the exhalation tube, however, may be free to move through the check valve, against the check valve's desired direction of flow. It will be understood that this valve could also be used in connection with other devices, structures, environments and the like. Further, this valve could be used in connection with other types of valves and not just check valves.

Although the substantially rigid top cap 12, as shown in FIGS. 1A through 1D, employs a downwardly extending, hollow, center cylinder 30 by which the substantially flexible membrane 14 may be attached to the center portion 24 of the substantially rigid portion 12 of the check valve, one of ordinary skill in the art will appreciate that other structures may be used. For instance, the center cylinder 30 may be upwardly extending or may not be hollow. Alternatively, the substantially rigid portion 12 of the check valve may simply include a hole through its center portion 24 through which a portion of the substantially flexible membrane 14 fits or is attached. A mechanical fastener, such as a rivet or screw, may also be used to attach the substantially flexible membrane 14 to the substantially rigid portion 12 of the check valve.

As discussed above and as shown in FIGS. 2A through 2D, the check valve may also include a substantially flexible membrane 14. The substantially flexible membrane 14 is preferably generally dome-shaped and which may be made of a flexible, bendable and/or elastic material such as rubber or silicon. The substantially flexible membrane 14 may include a center portion 32 by which the substantially flexible membrane can be connected to the substantially rigid top cap 12. The substantially flexible membrane 14 may also include an outer edge 34, sometimes referred to as a sealing edge 34, which may be designed to contact the sealing surface 18 of the substantially rigid top cap 12 when the check valve is in the closed position in order to prevent flow in the direction contrary to the check valve's desired direction of flow.

Still referring now to FIGS. 2A through 2D, the substantially flexible membrane 14 may also include a plurality of relatively thick sections 36, sometimes referred to as substantially flexible spokes 36. Advantageously, the substantially flexible spokes 36 may be created as part of the substantially flexible membrane 14. In addition, the substantially flexible spokes 36 may extend generally from the outer edge 34 to the center portion 32. The substantially flexible membrane 14 may also include a plurality of relatively thin sections 38, sometimes referred to as collapse zones 38, which may also be created as part of the substantially flexible membrane 14. Preferably, the collapse zones 38 are located in between the substantially flexible spokes 36 of the substantially flexible membrane 14.

The substantially flexible membrane 14 of the check valve shown in FIGS. 2A through 2D has five substantially flexible spokes 36 and five collapse zones 38. One of ordinary skill in the art, however, will appreciate that the substantially flexible membrane 14 may include any number of substantially flexible spokes 36, from no substantially flexible spokes 36 to a great many substantially flexible spokes. Furthermore, one of ordinary skill in the art will appreciate that the substantially flexible membrane 14 may include any number of collapse zones 38. For example, while the number of collapse zones 38 is preferably complimentary to the number of substantially flexible spokes 36, any number of substantially flexible spokes and/or collapse zones may also be used. Thus, the number of collapse zones 38 used is not limited to five and any number of number of collapse zones, from no collapse zones to a great many collapse zones, may be used.

By employing these relatively thick sections 36 and relatively thin sections 38 of the substantially flexible membrane 14, the overall thickness of the substantially flexible membrane may be decreased without, for example, compromising its structural stability. In addition, the relatively thick sections 36 of the substantially flexible membrane 14 may resist deformation and flexing more than the relatively thin sections 38 of the substantially flexible membrane. Thus, these relatively thick sections 36 may be capable of retaining the check valve's general dome shape and of holding the substantially flexible membrane 14 generally in place against the substantially rigid top cap 12. Significantly, this may help prevent failure of the check valve. The relatively thick sections 36 of the substantially flexible membrane 14 may also allow the relatively thin sections 38 of the substantially flexible membrane 14 to be thinner than the substantially flexible membrane 14 could be were it uniform in thickness.

The relatively thin sections 38 of the substantially flexible membrane 14 may deform or flex more easily than the relatively thick sections 36 of the substantially flexible membrane 14. This allows these relatively thin sections 38 to collapse when the pressure upstream from the check valve is only slightly greater than the pressure downstream from the check valve. This comparatively small pressure differential may cause the sealing edge 34 of the substantially flexible membrane 14 to separate from the sealing ring 18 of the substantially rigid top cap 12 with a relatively small amount of force or pressure. Accordingly, the relatively thin sections 38 may substantially reduce the cracking pressure of the check valve. It will be appreciated that the relatively thick sections 36 and relatively thin sections 38 of the substantially flexible membrane 14 could have other suitable shapes and configurations depending, for example, upon the intended use of the check valve.

As best seen in FIGS. 2A through 2D, the substantially flexible membrane 14 may also include a sleeve 40 extending downwardly from the center portion 32 of the substantially flexible membrane 14. This sleeve 40 may be sized and configured to surround or wrap around the center cylinder 30 of the substantially rigid top cap 12 in order to connect the center portion 32 of the substantially flexible membrane 14 to the center portion 24 of the substantially rigid top cap 12.

Although the substantially flexible membrane 14 of the check valve shown in the accompanying figures includes a downwardly extending, hollow sleeve 40 to attach the substantially flexible membrane 14 to the substantially rigid portion 12 of the check valve, those of ordinary skill in the art will appreciate that other structures may be used to achieve this same result. For instance, if the center cylinder 30 of the substantially rigid portion 12 of the check valve extends upwardly rather than downwardly, the substantially flexible membrane 14 may use an upwardly extending post that fits inside of the upwardly extending center cylinder. Similarly, if the substantially rigid portion 12 of the check valve includes a hole through its center portion 24 rather than a downwardly extending center cylinder 30, the substantially flexible membrane 14 may include a button or other protrusion which fits in or extends through this hole in order to attach the substantially flexible membrane 14 to the substantially rigid portion 12. A mechanical fastener, such as a rivet or screw, may also be used to attach the substantially flexible membrane 14 to the substantially rigid portion 12 of the check valve. Accordingly, other suitable devices or structures may be used to attach the substantially flexible membrane 14 to the substantially rigid portion 12 of the check valve.

Referring now to FIG. 3, the check valve 10 includes the substantially flexible membrane 14 connected to the substantially rigid top cap 12 so that each of the substantially flexible spokes 36 are positioned generally in between two of the substantially rigid spokes 22 and are generally aligned with one of the partial spokes 28. It will be appreciated that the substantially flexible membrane 14 may be connected to the substantially rigid top cap 12 in other desired orientations and configurations depending, for example, upon the intended use of the check valve.

In operation, when a positive pressure differential is applied to the check valve 10, the collapse zones 38 of the substantially flexible membrane 14 may initially collapse and separate at least a portion of the sealing edge 34 from the sealing ring 18 of the substantially rigid top cap 12. This may allow any suitable type of fluid to flow through the check valve. Depending upon the pressure differential, at least a portion of the substantially flexible spokes 36 may also separate from the sealing edge 34 from the sealing ring 18 of the substantially rigid top cap 12. Because the collapse zones 38 may deform or flex more than the substantially flexible spokes 36, the substantially flexible membrane 14 may generally resemble an umbrella. Thus, when the check valve is in the open position, the collapse zones 38 may bend or deform more than the substantially flexible spokes 36, which may give the substantially flexible membrane 14 the look of a closed or collapsed umbrella.

Advantageously, because only one collapse zone 38 need collapse in order to allow flow through the check valve, the size and configuration of the collapse zones 38 and/or substantially flexible spokes 36 may be manipulated to control the desired amount of fluid flow. For example, if the substantially flexible membrane 14 is manufactured so that the relatively thin sections 38 of the substantially flexible membrane 14 are generally consistent in thickness, then the collapse zones 38 may collapse at generally the same time and/or rate.

On the other hand, the thickness of the relatively thick sections 36 and/or the relatively thin sections 38 may be varied according to the desired use of the check valve. For instance, if substantial flow is needed or desired through the check valve, all collapse zones 38 may collapse even if the positive pressure differential is rather small.

As mentioned above, the check valve may also be a tracheostomy speaking valve. This tracheostomy speaking valve can be placed in the tracheostomy of a patient who, for instance, has an obstruction in his or her upper trachea which may interfere with normal breathing. This check valve may normally be in the closed position, but may opens when the patient inhales in order to allow air to enter the lungs through the traechea, possibly bypassing an obstruction. After the inspiration, the valve may close again. This may prevent air, exhaled or otherwise from leaking out of the tracheostomy speaking valve. Because exhaled air may not be able to leak out through the tracheostomy speaking valve, it may be forced further up the patient's trachea where it can pass the patient's vocal cords thereby allowing him or her to speak.

Figure 5A:
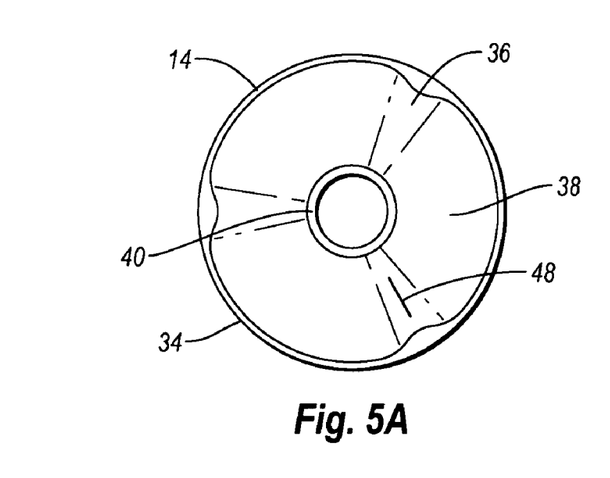
FIG. 5A is a bottom view of a portion of a still another exemplary embodiment of a check valve, illustrating a substantially flexible membrane.
Figure 5B:
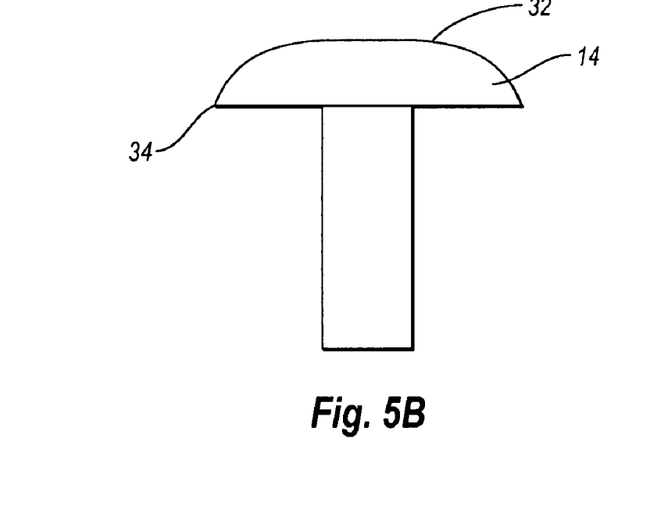
FIG. 5B is a side view of the substantially flexible membrane shown in FIG. 5A.
Figure 6:
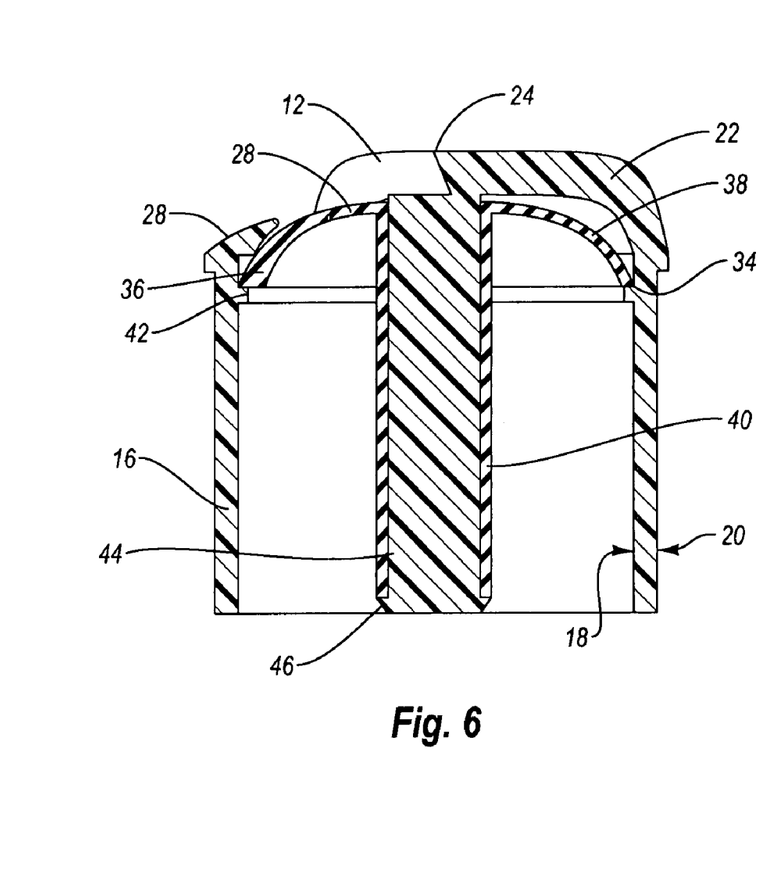
FIG. 6 is a side, cross-sectional view of a further exemplary embodiment of a check valve, illustrating a substantially flexible membrane attached to a substantially rigid top cap.

The tracheostomy speaking valve may be similar in many ways to the previously discussed inhalation valve for a snorkel. For example, the substantially rigid portion 12 of this exemplary embodiment illustrated in FIGS. 4A through 4D may be constructed from a strong and rigid material, such as plastic, in order to provide the tracheostomy speaking valve with structural support. This exemplary embodiment may also include a substantially flexible membrane 14. The substantially flexible membrane 14 is illustrated in FIGS. 5A and 5B and may be constructed from flexible or pliable materials, such as silicon or rubber. The substantially flexible membrane 14 is preferably sized and configured to flex or deform to allow the opening and closing of the tracheostomy speaking valve. The exemplary embodiment of the tracheostomy speaking valve with the substantially flexible membrane 14 connected to the substantially rigid top cap 12 is illustrated in FIG. 6.

In greater detail, as shown in FIGS. 4A through 4D, the substantially rigid portion 12 of the tracheostomy speaking valve may have a configuration and arrangement similar to the snorkel discussed above. For example, the substantially rigid portion 12 may include a substantially rigid base 16 with a sealing surface or sealing ring 18, an outer rim 20, a plurality of substantially rigid spokes 22, a plurality of gaps 26, and a plurality of partial spokes 28.

As shown in FIGS. 4A through 4D, the substantially rigid base may include a ridge or flange 42 that may extend inwardly from the sealing ring 18 of the substantially rigid base 16. This ridge 42 may be sized and configured to contact the outer edge 34 of the substantially flexible membrane 14 in order to keep the substantially flexible membrane 14 connected to and in position relative to the substantially rigid portion 12 of the tracheostomy speaking valve. For example, the ridge 42 may help prevent the substantially flexible membrane 14 from sliding off of or moving out of position relative to the substantially rigid portion 12. It will be appreciated that the substantially flexible membrane 14 may be attached to the substantially rigid base 16 in other suitable manners and methods.

Still referring to FIGS. 4A through 4D, the substantially rigid portion 12 of the tracheostomy speaking valve may also include a center post 44 extending downwardly from the center portion 24 of the substantially rigid portion 12. As with the center portion 30 of the inhalation valve for the snorkel, the center post 44 of the tracheostomy speaking valve may be used to attach the substantially flexible membrane 14 to the substantially rigid portion 12. The sleeve 40 of the substantially flexible membrane 14 may slide over and encompasses the center post 44 of the substantially rigid portion 12 so that the substantially flexible membrane 14 can stay in place relative to the substantially rigid portion 12.

The center post 44 of the tracheostomy speaking valve may also include a barb 46 at its lower end. This barb 46 may be sized and configured to contact the sleeve 40 of the substantially flexible membrane 14 in order to keep the substantially flexible membrane 14 connected to and in position relative to the substantially rigid portion 12 of the tracheostomy speaking valve. More specifically, the barb 46 may prevent the sleeve 40 of the substantially flexible membrane 14 from accidentally sliding off of the center post 44 of the substantially rigid portion 12.

Referring now to FIGS. 5A and 5B, the substantially flexible membrane 14 of the tracheostomy speaking valve may, like the inhalation valve for a snorkel described above, include an outer or sealing edge 34, a plurality of relatively thick sections or substantially flexible spokes 36, a plurality of relatively thin sections or collapse zones 38, and a sleeve 40. It will be appreciated that the tracheostomy speaking valve may also have other suitable configurations and arrangements depending, for example, upon the specific design and/or use of the tracheostomy speaking valve.

As shown in FIGS. 5A and 5B, the substantially flexible membrane 14 may also include a slit 48. In this exemplary embodiment, the slit 48 may be placed through one of the substantially flexible spokes 36. One of ordinary skill in the art, however, will appreciate that a plurality of slits 48 may be placed through the substantially flexible membrane 14 and that the slits 48 may be placed through the substantially flexible membrane 14 in locations other than through the substantially flexible spokes 36.

The slit 48 may serve to act as a pressure release in cases where there is a negative pressure differential of an undesirable or dangerous magnitude. For instance, the tracheostomy speaking valve may allow inhaled air through but prevents exhaled air from passing out. If, however, the patient using this tracheostomy speaking valve coughs, the force of the cough may damage the valve or could force the entire valve assembly out of its proper position within the throat of the patient. The slit 48, if properly sized and positioned, may allow some equalization of pressures in cases of an excessive, negative pressure differential without causing any significant leaking or backflow. It will be understood that any appropriate number and arrangement of slits 48 may be utilized depending, for example, upon the intended use of the tracheostomy speaking valve. It will also be understood that the slit 48 is not required.

Although this invention has been described in terms of certain preferred embodiments, other embodiments apparent to those of ordinary skill in the art are also within the scope of this invention. Accordingly, the scope of the invention is intended to be defined only by the claims which follow.

What is claimed is:

1. A check valve comprising:
   a flexible membrane having a generally dome-shaped configuration, the flexible membrane including a center portion and an outer edge, the flexible membrane comprising:
   one or more flexible spokes at least partially disposed between the center portion of the flexible membrane and the outer edge of the flexible membrane;
   one or more collapsible zones at least partially disposed between the center portion of the flexible membrane and the outer edge of the flexible membrane;

an elongated body with a length at least equal to a distance separating the outer edge and the center portion of the flexible membrane; and an opening extending through the center portion of the flexible membrane;

a support member constructed from a generally rigid material, the support member including a center portion that is sized and configured to be connected to the center portion of the flexible membrane, the support member including an outer rim, the support member comprising:

one or more spokes connecting the outer rim of the support member and the center portion of the support member; and an elongated body with a length at least equal to a distance separating the outer rim and the center portion of the support member; and an opening extending through the center portion of the support member, the opening in the center portion of the flexible membrane being at least partially aligned with the opening in the center portion of the support member to allow fluid to flow through the openings.

2. The check valve as in claim 1, wherein the elongated body of the support member has a generally cylindrical-shaped configuration and extends from the center portion of the support member; and wherein the elongated body of the flexible membrane extends from the center portion of the flexible membrane, the elongated body of the flexible membrane connected to the elongated body the support member.

3. The check valve as in claim 2, wherein the elongated body of the support member includes a center barb that is sized and configured to hold the center protrusion of the flexible membrane in a generally fixed position.

4. The check valve as in claim 1, wherein the support member includes a flange extending from the outer rim, the flange being sized and configured to hold the flexible membrane in a generally fixed position relative to the support member by contacting the outer edge of the flexible membrane.

5. The check valve as in claim 1, further comprising one or more partial spokes generally disposed between the outer rim and the center portion of the support member.

6. A check valve comprising:

a generally dome-shaped flexible membrane including a center portion, a sealing portion and a connecting portion at least partially disposed between the center portion and the sealing portion;

a generally dome-shaped rigid cap including a center support portion and a contact portion, the center support portion of the rigid cap being disposed at least proximate the center portion of the flexible membrane, the contact portion of the rigid cap being sized and configured to contact the sealing portion of the flexible membrane when the flexible membrane is in a closed position;

a rigid base of the rigid cap, the rigid base including one or more partial spokes extending towards the center portion of the rigid cap, the partial spokes including an end that is spaced apart from the center portion of the rigid cap;

one or more flexible spokes at least partially disposed between an outer edge of the flexible membrane and the center portion of the flexible membrane; and one or more collapsible zones at least partially disposed between an outer edge of the flexible membrane and the center portion of the flexible membrane.

7. The check valve as in claim 6, further comprising a projection extending from a connecting portion of the rigid cap, the projection being sized and configured to help maintain the center portion of the flexible membrane in a generally fixed position relative to the rigid cap.

8. The check valve as in claim 6, further comprising a rigid base of the rigid cap, the rigid base being connected to the center portion of the rigid cap by one or more spokes.

9. The check valve as in claim 6, further comprising a rigid base of the rigid cap; and further comprising one or more spokes extending from the rigid base to the center support portion of the rigid cap, the spokes having a generally dome-shaped configuration with an arch-shaped outer surface and an arch-shaped inner surface.

10. The check valve as in claim 6, wherein the rigid cap includes a rigid base and a flange extending from the rigid base;

wherein the flexible membrane includes an outer edge; and
wherein the flange of the rigid cap is sized and configured to hold the flexible membrane in a relatively fixed position by contacting the outer edge of the flexible membrane.

11. The check valve as in claim 6, further comprising one or more openings in the flexible membrane.

12. A check valve that helps regulate fluid flow by allowing fluid flow when a positive pressure differential that is greater than a predetermined amount is applied to the check valve, the check valve comprising:

a substantially flexible portion that is sized and configured to allow fluid to flow in a first direction when the positive pressure differential is greater than the predetermined amount, the substantially flexible portion having a generally dome-shaped configuration, the substantially flexible portion comprising:

a sealing portion that is movable between an open position and a closed position; and a center portion; and an opening in the center portion that is sized and configured to allow fluid to a direction generally opposite the first direction; and a substantially rigid portion that is sized and configured to at least partially position and control movement of the substantially flexible portion, the substantially rigid portion having a generally dome-shaped configuration, the substantially rigid portion comprising:

a contact portion that is sized and configured to contact the sealing portion of the substantially flexible portion when the sealing portion is in the closed position;

a center support structure that supports the center portion of the substantially flexible portion in a generally fixed position; and a plurality of spokes connecting the contact portion and the center support structure, each of the spokes having a curved inner surface that engages an outer surface of the generally dome-shaped substantially flexible portion when the substantially flexible portion is in a closed position, the inner surface of each of the spokes being sized and configured to help maintain the substantially flexible portion in the generally dome-shaped configuration when the substantially flexible portion is in the closed position.

13. The check valve as in claim 12, wherein the check valve is used as an inhalation valve for a snorkel.

14. The check valve as in claim 12, wherein the sealing portion forms at least a portion of an outer periphery of the substantially flexible portion.

15. The check valve as in claim 12, wherein fluid flow in the first direction is generally directed towards an outer surface of the dome.

16. The check valve as in claim 12, wherein at least a portion of the substantially flexible portion flexes and/or deforms to create an opening between the sealing portion and the contact portion when a positive pressure differential greater than a predetermined amount is applied to the check valve.

17. The check valve as in claim 12, wherein at least a portion of the sealing portion of the substantially flexible portion moves inwardly and away from the contact portion of the substantially rigid portion to create an opening to allow fluid flow when a positive pressure differential greater than a predetermined amount is applied to the check valve.

18. The check valve as in claim 12, wherein the substantially flexible portion includes at least one portion with different flexibility characteristics to allow different portions of the substantially flexible portion to move at different pressure differentials.

19. The check valve as in claim 12, wherein at least one portion of the substantially flexible portion has increased flexibility and at least one portion of the substantially flexible portion has decreased flexibility to allow different portions of the substantially flexible portion to move at different pressure differentials.

20. The check valve as in claim 12, wherein at least one portion of the substantially flexible portion has decreased thickness to create a portion with increased flexibility and at least one portion of the substantially flexible portion has increased thickness to crease a portion with decreased flexibility to allow different portions of the substantially flexible portion to move at different pressure differentials.

21. The check valve as in claim 12, wherein the contact portion of the substantially rigid portion forms at least a portion of a sealing ring.

22. The check valve as in claim 12, further comprising one or more connecting members that connect the contact portion and the center support structure of the substantially rigid portion.

23. The check valve as in claim 12, wherein the inner surface of each of the spokes, an outer surface of the substantially flexible portion and an inner surface of the substantially flexible portion have a radius of curvature that are at least substantially the same.

24. The check valve as in claim 12, further comprising a sleeve of the substantially flexible portion, the sleeve being at least partially connected to the center support structure of the substantially rigid portion.

25. A check valve that helps regulate fluid flow by allowing fluid flow when a positive pressure differential that is greater than a predetermined amount is applied to the check valve, the check valve comprising:
 a generally dome-shaped rigid portion comprising: a base having a generally circular configuration;
  a plurality of spokes extending upwardly and inwardly from the base, each of the spokes having a curved inner surface; and
  a support structure that is spaced apart from the base by a distance, at least one of the plurality of spokes connecting the base and the support structure; and
  an opening in a center portion of the support structure; and
 a generally dome-shaped flexible membrane that is at least substantially disposed within the generally dome-shaped rigid portion, the flexible membrane being sized and configured to allow fluid to flow in a first direction when the positive pressure differential is greater than the predetermined amount, the flexible membrane comprising:
  a sealing edge that is capable of moving between an open position and a closed position, the sealing edge being sized and configured to contact the base of the rigid portion when the sealing edge is in the closed position;
  a center portion that is supported by the support structure of the rigid portion in a generally fixed position;
  an opening in the center portion of the flexible membrane, the opening in the center portion of the flexible membrane being at least partially aligned with the opening in the center portion of the support structure to allow fluid to flow through the openings; and
  an outer surface that engages the curved inner surface of the spokes when the flexible membrane is in a closed position, the inner surface of the spokes being sized and configured to help maintain the flexible membrane in the generally dome-shaped configuration when the flexible membrane is in the closed position.

26. The check valve as in claim 25, wherein the check valve is used as a valve for a snorkel.

27. The check valve as in claim 25, wherein the check valve is used as a tracheostomy valve.

28. A check valve comprising:
 a flexible membrane having a generally dome-shaped configuration, the flexible membrane including a center portion and an outer edge, the flexible membrane comprising:
  one or more flexible spokes at least partially disposed between the center portion of the flexible membrane and the outer edge of the flexible membrane;
  one or more collapsible zones at least partially disposed between the center portion of the flexible membrane and the outer edge of the flexible membrane; and
  an elongated body with a length at least equal to a distance separating the outer edge and the center portion of the flexible membrane;
 a support member constructed from a generally rigid material, the support member including a center portion that is sized and configured to be connected to the center portion of the flexible membrane, the support member including an outer rim; the support member comprising:
  one or more spokes connecting the outer rim of the support member and the center portion of the support member;
  an elongated body with a length at least equal to a distance separating the outer rim and the center portion of the support member; and
  a flange extending from the outer rim, the flange being sized and configured to hold the flexible membrane in a generally fixed position relative to the support member by contacting the outer edge of the flexible membrane.

29. The check valve as in claim 28, wherein the elongated body of the support member has a generally cylindrical-shaped configuration and extends from the center portion of the support member; and
 wherein the elongated body of the flexible membrane extends from the center portion of the flexible membrane, the elongated body of the flexible membrane connected to the elongated body of the support member.

30. The check valve as in claim 28, further comprising an opening extending through the center portion of the support member; and
 an opening extending through the center portion of the flexible membrane, the opening in the center portion of the flexible membrane being at least partially aligned with the opening in the center portion of the support member to allow fluid to flow through the openings.

* * * * *